US008287880B2

(12) United States Patent
Chen et al.

(10) Patent No.: US 8,287,880 B2
(45) Date of Patent: *Oct. 16, 2012

(54) LIPIDATED VACCINE AGAINST DENGUE VIRUS INFECTION

(75) Inventors: Hsin-Wei Chen, Miaoli County (TW); Chih-Hsiang Leng, Miaoli County (TW); Shih-Jen Liu, Miaoli County (TW); Pele Choi-Sing Chong, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 210 days.

This patent is subject to a terminal disclaimer.

(21) Appl. No.: 12/787,539

(22) Filed: May 26, 2010

(65) Prior Publication Data

US 2010/0303849 A1    Dec. 2, 2010

Related U.S. Application Data

(60) Provisional application No. 61/183,277, filed on Jun. 2, 2009.

(51) Int. Cl.
*A61K 39/295* (2006.01)
*A61K 39/12* (2006.01)

(52) U.S. Cl. ............... 424/201.1; 424/192.1; 424/218.1; 435/5

(58) Field of Classification Search .................. None
See application file for complete search history.

(56) References Cited

U.S. PATENT DOCUMENTS

| | | | |
|---|---|---|---|
| 4,745,069 A | 5/1988 | Mayne et al. | |
| 5,942,236 A | 8/1999 | Lobert et al. | |
| 6,013,258 A | 1/2000 | Urban et al. | |
| 6,183,746 B1 | 2/2001 | Urban et al. | |
| 6,361,966 B1 | 3/2002 | Walker et al. | |
| 6,538,118 B1 | 3/2003 | Huebner et al. | |
| 6,582,704 B2 | 6/2003 | Urban et al. | |
| 6,936,263 B2 | 8/2005 | Revets et al. | |
| 7,097,843 B2 | 8/2006 | Urban et al. | |
| 7,235,243 B2 | 6/2007 | Becker et al. | |
| 7,314,629 B2 | 1/2008 | Zagury et al. | |
| 7,569,225 B2 | 8/2009 | Jackson et al. | |
| 7,833,776 B2 * | 11/2010 | Leng et al. ............... | 435/252.33 |
| 2005/0276813 A1 | 12/2005 | Muhlradt et al. | |
| 2005/0281835 A1 | 12/2005 | Yang | |
| 2009/0074781 A1 | 3/2009 | Chen et al. | |
| 2009/0081253 A1 | 3/2009 | Hanon et al. | |
| 2009/0176273 A1 | 7/2009 | Leng et al. | |
| 2009/0221499 A1 | 9/2009 | Leng et al. | |
| 2010/0303849 A1 | 12/2010 | Chen et al. | |
| 2010/0322953 A1 | 12/2010 | Leng et al. | |
| 2012/0041179 A1 | 2/2012 | Hsieh et al. | |

FOREIGN PATENT DOCUMENTS

| | | |
|---|---|---|
| CA | 2183416 | 8/1995 |
| CA | 2706101 | 6/2009 |
| CN | 1793335 | 6/2006 |
| EP | 1612218 | 1/2006 |
| EP | 2058002 | 5/2009 |
| GB | 2001/029236 | 4/2011 |
| JP | 2008-113608 | 5/2008 |
| WO | 92/05248 | 4/1992 |
| WO | 92-16636 | 10/1992 |
| WO | 99/10375 | 3/1999 |
| WO | 99/57280 | 11/1999 |
| WO | 2004/052395 | 6/2004 |
| WO | 2007/199896 | 10/2007 |
| WO | 2008/079372 | 7/2008 |
| WO | 2010/148496 | 12/2010 |

OTHER PUBLICATIONS

Crill et al., J. Virology, 2001, 75(16):7769-7773.*
Babaeipour, Valiollah, et al. "Enhancement of human granulocyte-colony stimulating factor production in recombinant *E. coli* using batch cultivation" Bioprocess Biosyst Eng (2010) pp. 591-598.
Chen, H-W. et al. A novel technology for the production of a heterologous lipoprotein immunogen in high yield has implications for the field of vaccine design. Vaccine. Epub: IS Jan. 15, 2009. vol. 27, pp. 1400-1409.
Chiung-Yi Huang. "Potential Treatment of Human Papillomavirus Associated Tumors Using Recombinant Inactive-E7 Lipoproteins." Electronic Theses & Dissertations Services; Master Programs of Life Sciences, Aug. 24, 2009. pp. 1-5.
Cullen et al., "Construction and Evaluation of a Plasmid Vector for the Expression of Recombinant Lipoproteins in *Escherichia coli*," Plasmid 49: 18-29 (2003).
De et al., "Purification and Characterization of *Streptococcis pneumoniae* palmitoylated and pneumococcal surface adhesion A expressed in *Escherichia coli*," Vaccine: 18: 1811-1821 (2000).
Dumon-Seignovert et al., The toxicity of recombinant proteins in *Escherichia coli*: a comparison of overexpression in BL21 (DE3), C41 (DE3), and C43(DE3)., Protein Expression and Purification, vol. 37, Issue 1, Sep. 2004, pp. 203-206.
Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.
Green et al., The e(P4) Outer membrane Protein of *Haemophilus influenzae*: biologic activity of Anti-e Serum and Cloning and Sequencing of the Structural Gene., Infection and Immunity, 1991, vol. 59, pp. 3191-3198.
Hsu, C-A. et at. Immunoproteomic identification of the hypothetical protein NMB1468 as a novel lipoprotein ubiquitous in *Neisseria meningitidis* with vaccine potential. Proteomics. 2008. vol. 8, pp. 2115-2125.
Kamalakkannan et al., "Bacterial Lipid Modification of Proteins for Novel Protein Engineering Applications," Protein, Engineering, Design & Selection 17(10): 721-729 (2004).
Legrain et al., "Production of Lipidated Meningococcal Transferrin Binding Protein 2 in *Escherichia coli*" Protein Expression and Purification 6:570-578 (1995).

(Continued)

*Primary Examiner* — Stacy B. Chen
(74) *Attorney, Agent, or Firm* — Occhiuti Rohlicek & Tsao LLP

(57) ABSTRACT

Disclosed are immunogenic composition, fusion proteins, and related methods for inducing immune response to dengue virus infection.

19 Claims, 3 Drawing Sheets

OTHER PUBLICATIONS

Liu, et al. "Structure of the Human Papillomavirus E7 Oncoprotein and its Mechanism for Inactivation of the Retinoblastoma Tumor Suppressor", 1. Biol. Chem., Jan. 2006. vol. 281, pp. 578-586.

Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998. pp. 2103-2109.

Sung, et al. Biochemical characterizations of *Escherichia coli*-expressed protective antigen Ag473 of *Neisseria meningitides* group B., *Vaccine*. vol. 28(51) Nov. 29, 2010, pp. 8175-8182.

ExPASy—PeptideCutter http://web.expasy.ort/cgi-bin/peptide_cutter/peptidecutter.pl (Accessed Mar. 7, 2012).

Shu, et al. Core Structure of the Outer membrane Lipoprotein from *Escherichia coli* at 1.9A Resolution, (2000) vol. 299, pp. 1101-11112.

Rezwan, et al. "Lipoprotein synthesis in mycobacteria" *Microbiology*. Mar. 2007, vol. 153, pp. 652-658.

Wikman, et al. General strategies for efficient adjuvant incorporation of recombinant subunit immunogents. *Vaccine*. (2005), vol. 23, pp. 2331-2335.

Cote-Sierra, et al. "A New Membrane-Bound Oprl Lipoprotien Expression Vector High Prodcution of Heterologous Fusion Proteins in Gram (−) Bacteria and the Implications for Oral Vaccination" *Gene* (1998) vol. 221, pp. 25-34.

Chen, W., et al. "Induction of cytotoxic T-lymphocytes and antitumor activity by a liposomal lipopeptide vaccine" *Mol. Pharm.* vol. 5, No. 3 (2008) pp. 464-471.

Jackson, D.C., et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.

Masconi, et al. "Structural Basis for the Immunogenic Properties of the Meningococcal Vaccine Candidate LP2086" The Journal of Biological Chemistry, vol. 284, No. 13, pp. 8738-8746 (Mar. 27, 2009).

Sivashanmugam, Arun, et al. "Practical protocols for production of very high yields of recombinant proteins using *Escherichia coli*" Protein Science vol. 18, pp. 936-948 (2009).

* cited by examiner

LIPIDATED VACCINE AGAINST DENGUE VIRUS INFECTION

RELATED APPLICATION

This application claims priority of U.S. Provisional Application No. 61/183,277, filed on Jun. 2, 2009. The prior application is incorporated herein by reference in its entirety.

BACKGROUND

Dengue virus is a member of the Flaviviridae virus family, which includes four serotypes, DEN-1, DEN-2, DEN-3, and DEN-4. Infection of dengue virus leads to dengue fever, which is characterized by sudden onset of severe headache, muscle and joint pains, fever, and rash. A number of dengue epidemics occurred during the past. According to the World Health Organization, there are an estimated 50 million cases of dengue fever with 500,000 cases of dengue hemorrhagic fever requiring hospitalization each year. Vaccination is considered to be the most effective and efficient approach to prevent Dengue virus infection. However, despite decades of research, a safe and effective dengue vaccine is still not available. There is a need for such a safe and effective dengue vaccine.

SUMMARY

This invention relates to immunogenic compositions, such as vaccines, against Dengue virus infection.

One aspect of the invention features an immunogenic composition having a recombinant fusion protein that has a first segment having a lipidating sequence and a second segment having the sequence of a Dengue viral protein fragment. The fusion protein or the dengue viral protein fragment, once administered to a subject, can induce antibodies against dengue virus, e.g., cross-neutralizing antibodies against four serotypes of dengue virus. In one embodiment, the lipidating sequence includes at least 40 residues from the N-terminus of an Ag473 protein (shown below). The immunogenic composition optionally further contains a pharmaceutically acceptable adjuvant.

The Dengue viral protein fragment can be any immunogenic or antigenic protein fragment from a Dengue virus. In a preferred embodiment, the Dengue viral protein fragment includes the sequence of consensus envelope protein domain III (cED III). The amino acid and related nucleic acid coding sequences of this cED III (SEQ ID NOs: 6 and 7, respectively) are listed below:

```
                                                       (SEQ ID NO: 6)
          Lys Gly Met Ser Tyr Ala Met Cys Thr Gly Lys Phe Lys Leu Glu
          1               5                   10                  15

Lys Glu Val Ala Glu Thr Gln His Gly Thr Ile Leu Ile Lys Val
                          20                  25                  30

Lys Tyr Glu Gly Asp Gly Ala Pro Cys Lys Ile Pro Phe Glu Ile
                              35                  40                  45

Gln Asp Val Glu Lys Lys His Val Asn Gly Arg Leu Ile Thr Ala
                              50                  55                  60

Asn Pro Ile Val Thr Asp Lys Glu Ser Pro Val Asn Ile Glu Ala
                              65                  70                  75

Glu Pro Pro Phe Gly Asp Ser Tyr Ile Val Ile Gly Val Gly Asp
                              80                  85                  90

Lys Ala Leu Lys Leu Asn Trp Phe Lys Lys Gly Ser Ser
                              95                  100

(SEQ ID NO: 7)
            1  AAA GGC ATG AGC TAT GCG ATG TGC ACC G-
               GC AAA TTT AAA CTG GAA

46  AAA GAA GTG GCG GAA ACC CAG CAT G-
               GC ACC ATT CTG ATT AAA GTG

91  AAA TAT GAA GGC GAT GGC GCG CCG TG-
               C AAA ATT CCG TTT GAA ATT

136  CAG GAT GTG GAA AAA AAA CAT GTG AAC G-
               GC CGT CTG ATT ACC GCG

181  AAC CCG ATT GTG ACC GAT AAA GAA AGC-
               CCG GTG AAC ATT GAA GCG

226  GAA CCG CCG TTT GGC GAT AGC TAT AT-
               T GTG ATT GGC GTG GGC GAT

271  AAA GCG CTG AAA CTG AAC TGG TTT AAA AAA GGC AGC AGC
```

Another aspect of this invention features an isolated fusion protein that includes a first segment having a lipidating sequence and a second segment having the sequence of a dengue viral protein fragment. The first segment can be located at the N-terminus to the second segment of the fusion protein. In one embodiment, the fusion protein is lipidated. The lipidating sequence can include at least 40 residues from the N-terminus of Ag473 (e.g., SEQ ID NOs: 20-22 shown below). In one embodiment, the Dengue viral protein fragment includes the sequence of envelope protein domain III (SEQ ID NO: 6) or the corresponding sequence of DEN-1, DEN-2, DEN-3, and DEN-4.

An isolated protein or polypeptide refers to a protein or polypeptide substantially free from naturally associated molecules, i.e., it is at least 75% (i.e., any number between 75% and 100%, inclusive) pure by dry weight. Purity can be measured by any appropriate standard method, e.g., by column chromatography, polyacrylamide gel electrophoresis, or HPLC analysis. An isolated polypeptide or protein can be purified from a natural source, produced by recombinant DNA techniques, or by chemical methods.

The invention also features an isolated nucleic acid that contains a sequence encoding the above-described fusion protein. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide or protein of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., T7 promoter, cauliflower mosaic virus 35S promoter sequences or polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide/protein of this invention.

Also within the scope of this invention is a host cell that contains the above-described nucleic acid. Examples include *E. coli* cells, insect cells (e.g., using baculovirus expression vectors), plant cells, yeast cells, or mammalian cells. See e.g., Goeddel, (1990) Gene Expression Technology: Methods in Enzymology 185, Academic Press, San Diego, Calif.

To produce a fusion protein/polypeptide of this invention, one can culture a host cell in a medium under conditions permitting expression of the fusion protein/polypeptide encoded by a nucleic acid of this invention, and purify the fusion protein/polypeptide from the cultured cell or the medium of the cell. Alternatively, the nucleic acid of this invention can be transcribed and translated in vitro, for example, using T7 promoter regulatory sequences and T7 polymerase in cell lysate from, e.g., *E. coli*. The lipidated fusion protein can include, from N-terminus to C-terminus, D1 fragment of Ag473 and dengue envelope protein domain III.

In another aspect, the invention features a method of inducing an immune response to dengue virus infection. The method includes the step of administering to a subject in need thereof an effective amount of the above-described immunogenic composition. The immunogenic composition can be formulated or not formulated with an adjuvant.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
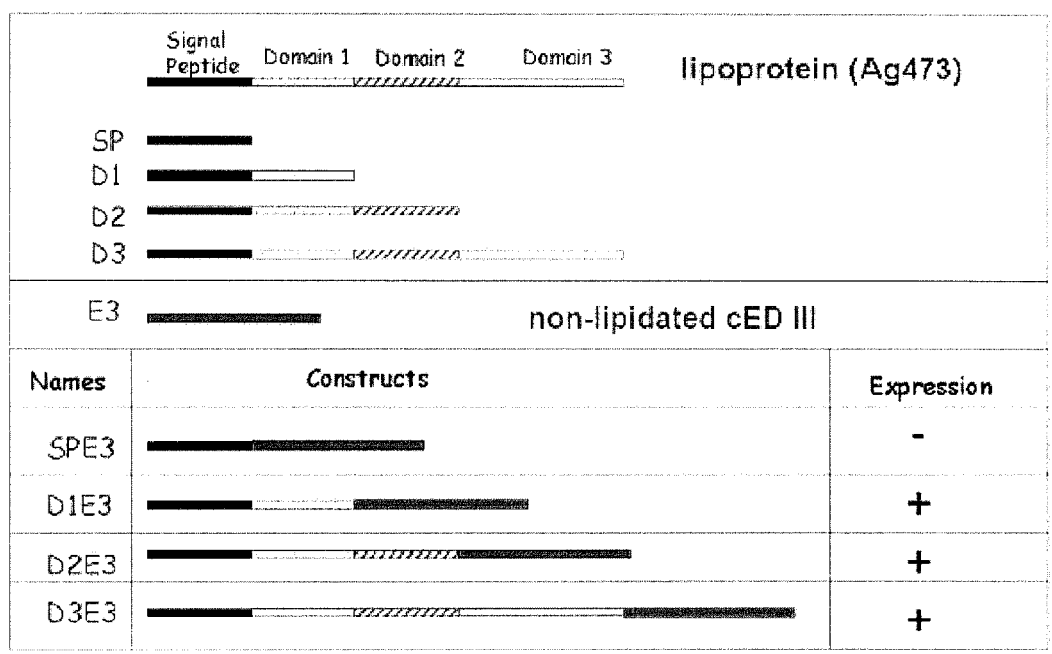
FIG. 1 is a diagram showing SP and Domains 1-3 in lipoprotein Ag473 and Ag473 fragments SP, D1, D2, and D3 (upper panel), as well as dengue virus cED III antigen (bottom panel), which is not lipidated in native state.
Figure 2:
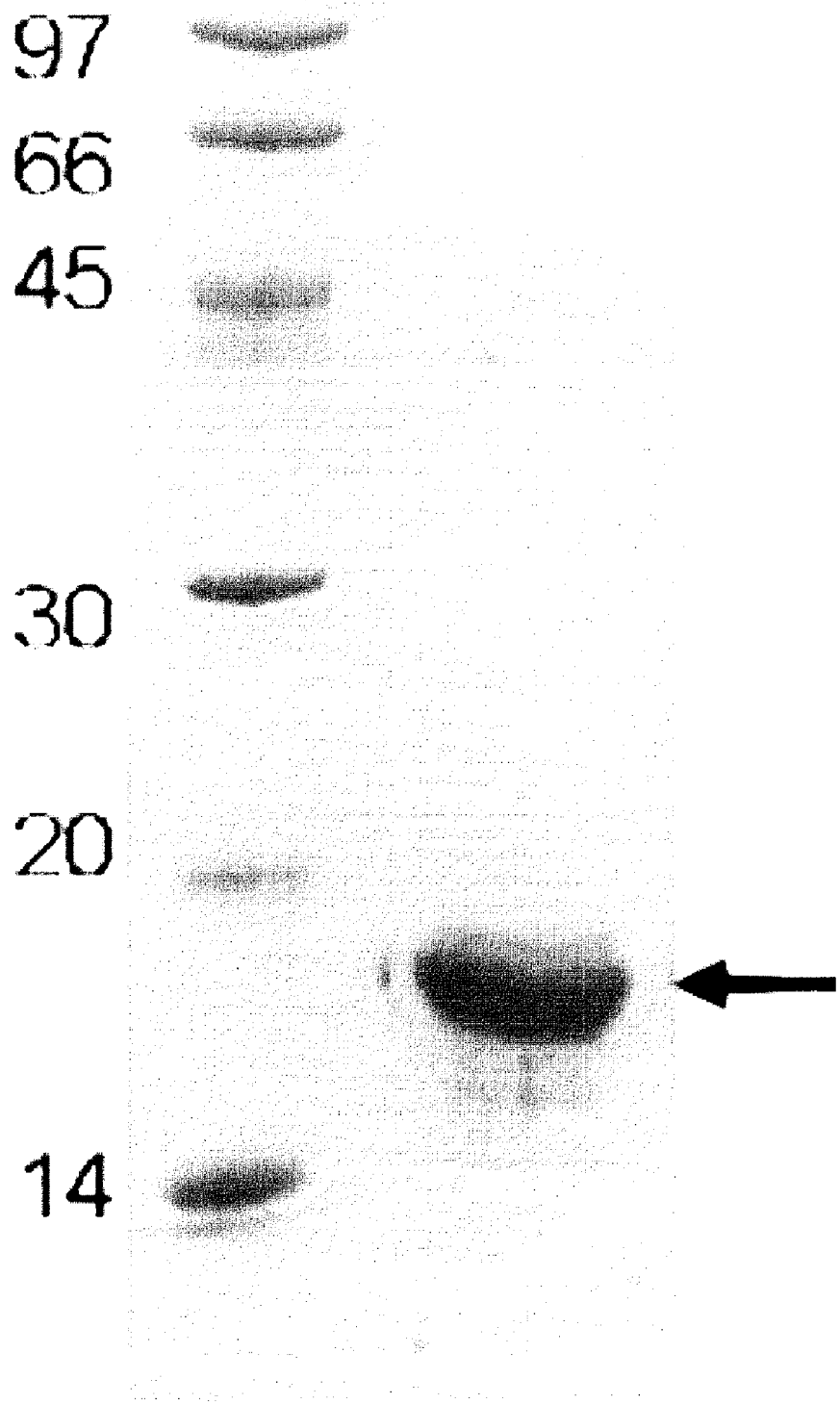
FIG. 2 is a photograph showing the electrophoretic mobility of purified rlipo-cED III. The arrow indicates the positions of recombinant rlipo-cED III.

This invention is based, at least in part, on the unexpected discoveries that a lipidating sequence of Ag473 led to lipidatation of a fusion protein having the lipidating sequence and a Dengue virus protein, and that the lipidated a fusion protein was much more immunogenic than the Dengue virus protein with no lipidation.

Accordingly, the present invention features an immunogenic composition, such as vaccines, against Dengue virus infection. As mentioned above, the immunogenic compositions contain a recombinant fusion protein. The fusion protein has a first segment having a lipidating sequence and a second segment having the sequence of a dengue viral protein fragment. The dengue viral protein fragment can induce, in a subject, antibodies against dengue virus, such as cross-neutralizing antibodies against four serotypes of dengue virus.

An "antibody" refers to an immunoglobulin molecule or at least one immunologically active portion of an immunoglobulin molecule that has a specific amino acid sequence and binds only to an antigen or a group of antigens that are closely related. Examples of "antibodies" include IgG, IgM, IgA, IgD and IgE. Examples of immunologically active portions of immunoglobulin molecules include Fab and F(ab)'.sub.2 fragments which can be generated by treating the antibody with an enzyme such as pepsin. An "antibody" can be a monoclonal antibody or a polyclonal antibody. The term "monoclonal antibody" refers to a population of antibody molecules that contains only one species of an antigen binding site and that is capable of immunoreacting with a particular epitope. The term "polyclonal antibody" refers to a population of antibody molecules that contains more than one species of antigen binding sites and that is capable of immunoreacting with more than one epitope on the polypeptide.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, etc. In a preferred embodiment, the subject is a human. In another embodiment, the subject is an experimental animal or animal suitable as a disease model.

The Dengue viral protein fragment can be any immunogenic or antigenic protein fragment from a Dengue virus. In one embodiment, the dengue viral protein is fragment of a Dengue envelope protein. The Dengue envelope protein includes three domains (I, II, and III). It is believed that domain III (E3) plays an important role in receptor recognition. In the previous U.S. patent application Ser. No. 12/156,908, the content of which is incorporated herein by reference in its entirety, a consensus envelope protein domain III (cED III) was developed as a vaccine candidate. It was found that cED III was able to induce neutralizing antibody against four serotype of dengue virus (Leng, C H, et al., Mcrobe and Infection 11 (2009) 288-295). A "consensus sequence" refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. Various software programs known in the art can be used to determine a consensus sequence.

The present invention discloses a fusion protein of one of the above-mentioned cED I, II, or III with the N-terminal portion of Ag473 for the production of a recombinant lipo-cED I, II, or III in high yield in an *E. coli* expression system. It was unexpected that the recombinant fusion protein alone (i.e., in the absence of any adjuvant) can induce cross-neutralization antibody responses against four serotypes of dengue virus.

The above-mentioned Ag473 is a *Neisseria meningitidis* lipoprotein consisting of four domains, SP and Domains 1-3. See FIG. 1, upper panel. Shown below is the candidate lipidating sequence in the amino acid sequence of this protein with the four domains identified:

```
Met Lys Lys Leu Leu Ile Ala Ala Met Met Ala Ala

Ala Leu Ala Ala Cys Ser Gln Glu Ala Lys Gln Glu

Val Lys Glu Ala Val Gln Ala Val Glu Ser Asp Val

Lys Asp Thr Ala Ala Ser Ala Ala Glu Ser Ala Ala

Ser Ala Val Glu Glu Ala Lys Asp Gln Val Lys Asp

Ala Ala Ala Asp Ala Lys Ala Ser Ala Glu Glu Ala

Val Thr Glu Ala Lys Glu Ala Val Thr Glu Ala Lys

Glu Ala Val Thr Glu Ala Lys Glu Ala Val Thr Glu

Ala Ala Lys Asp Thr Leu Asn Lys Ala Ala Asp Ala

Thr Gln Glu Ala Ala Asp Lys Met Lys Asp Ala Ala

Lys (SEQ ID NO: 1)
```

SP: amino acid residues 1-17 in SEQ ID NO:1 (underlined, SEQ ID NO: 8)

Domain 1: amino acid residues 18-40 in SEQ ID NO:1 (highlited, SEQ ID NO: 9)
Domain 2: amino acid residues 41-71 in SEQ ID NO:1 (bold face, SEQ ID NO: 10)
Domain 3: amino acid residues 72-121 in SEQ ID NO:1 (italic, SEQ ID NO: 11)

Listed below are the amino acid and nucleic acid of fusion proteins of E3 from Dengue-1, Dengue-2, Dengue-3, and Dengue-4 viruses (SEQ ID NOs: 12-19). The SP-Domain 1 sequence (D1 fragment, aa 1-40) and E3 sequence (aa 43-145; SEQ ID NOs: 23-26) in each fusion protein are underlined.

Lipo-DEN-1 Amino acid sequence (SEQ ID NO: 12):
Met Lys Lys Leu Leu Ile Ala Ala Met Met Ala Ala Ala
Leu Ala Ala Cys Ser Gln Glu Ala Lys Gln Glu Val Lys
Glu Ala Val Gln Ala Val Glu Ser Asp Val Lys Asp Thr
Ala Gly Ser Lys Gly Met Ser Tyr Val Met Cys Thr Gly
Ser Phe Lys Leu Glu Lys Glu Val Ala Glu Thr Gln His
Gly Thr Val Leu Val Gln Val Lys Tyr Glu Gly Thr Asp
Ala Pro Cys Lys Ile Pro Phe Ser Ser Gln Asp Glu Lys
Gly Val Thr Gln Asn Gly Arg Leu Ile Thr Ala Asn Pro
Ile Val Thr Asp Lys Glu Lys Pro Val Asn Ile Glu Ala
Glu Pro Pro Phe Gly Glu Ser Tyr Ile Val Val Gly Ala
Gly Glu Lys Ala Leu Lys Leu Ser Trp Phe Lys Lys Gly
Ser Ser Lipo-DEN-1 DNA sequence (SEQ ID NO: 13):
ATG AAA AAA CTG CTG ATT GCG GCG ATG ATG GCG GCG GCG
CTG GCG GCG TGC AGC CAG GAA GCG AAA CAG GAA GTG AAA
GAA GCG GTG CAG GCG GTG GAA AGC GAT GTG AAA GAT ACC
GCG GGA TTC AAA GGC ATG AGC TAT GTG ATG TGC ACC GGC
AGC TTT AAA CTG GAA AAA GAA GTG GCG GAA ACC CAG CAT
GGC ACC GTG CTG GTG CAG GTG AAA TAT GAA GGC ACC GAT
GCG CCG TGC AAA ATT CCG TTT AGC AGC CAG GAT GAA AAA
GGC GTG ACC CAG AAC GGC CGT CTG ATT ACC GCG AAC CCG
ATT GTG ACC GAT AAA GAA AAA CCG GTG AAC ATT GAA GCG
GAA CCG CCG TTT GGC GAA AGC TAT ATT GTG GTG GGC GCG
GGC GAA AAA GCG CTG AAA CTG AGC TGG TTT AAA AAA GGC
AGC AGC Lipo-DEN-2 Amino acid sequence (SEQ ID NO: 14):
Met Lys Lys Leu Leu Ile Ala Ala Met Met Ala Ala Ala
Leu Ala Ala Cys Ser Gln Glu Ala Lys Gln Glu Val Lys
Glu Ala Val Gln Ala Val Glu Ser Asp Val Lys Asp Thr
Ala Gly Ser Lys Gly Met Ser Tyr Ser Met Cys Thr Gly
Lys Phe Lys Val Val Lys Glu Ile Ala Glu Thr Gln His
Gly Thr Ile Val Ile Arg Val Gln Tyr Glu Gly Asp Gly
Ser Pro Cys Lys Ile Pro Phe Glu Ile Met Asp Leu Glu
Lys Arg His Val Leu Gly Arg Leu Ile Thr Val Asn Pro
Ile Val Thr Glu Lys Asp Ser Pro Val Asn Ile Glu Ala
Glu Pro Pro Phe Gly Asp Ser Tyr Ile Ile Ile Gly Val
Glu Pro Gly Gln Leu Lys Leu Asn Trp Phe Lys Lys Gly
Ser Ser Lipo-DEN-2 DNA sequence (SEQ ID NO: 15):
ATG AAA AAA CTG CTG ATT GCG GCG ATG ATG GCG GCG GCG
CTG GCG GCG TGC AGC CAG GAA GCG AAA CAG GAA GTG AAA
GAA GCG GTG CAG GCG GTG GAA AGC GAT GTG AAA GAT ACC
GCG GGA TTC AAA GGC ATG AGC TAT AGC ATG TGC ACC GGC
AAA TTT AAA GTG GTG AAA GAA ATT GCG GAA ACC CAG CAT
GGC ACC ATT GTG ATT CGT GTG CAG TAT GAA GGC GAT GGC
AGC CCG TGC AAA ATT CCG TTT GAA ATT ATG GAT CTG GAA
AAA CGT CAT GTG CTG GGC CGT CTG ATT ACC GTG AAC CCG
ATT GTG ACC GAA AAA GAT AGC CCG GTG AAC ATT GAA GCG
GAA CCG CCG TTT GGC GAT AGC TAT ATT ATT ATT GGC GTG
GAA CCG GGC CAG CTG AAA CTG AAC TGG TTT AAA AAA GGC
AGC AGC Lipo-DEN-3 Amino acid sequence (SEQ ID NO: 16):
Met Lys Lys Leu Leu Ile Ala Ala Met Met Ala Ala Ala
Leu Ala Ala Cys Ser Gln Glu Ala Lys Gln Glu Val Lys
Glu Ala Val Gln Ala Val Glu Ser Asp Val Lys Asp Thr
Ala Gly Ser Lys Gly Met Ser Tyr Ala Met Cys Leu Asn
Thr Phe Val Leu Lys Lys Glu Val Ser Glu Thr Gln His
Gly Thr Ile Leu Ile Lys Val Glu Tyr Lys Gly Glu Asp
Ala Pro Cys Lys Ile Pro Phe Ser Thr Glu Asp Gly Gln
Gly Lys Ala His Asn Gly Arg Leu Ile Thr Ala Asn Pro -continued
```
Val Val Thr Lys Lys Glu Glu Pro Val Asn Ile Glu Ala
Glu Pro Pro Phe Gly Glu Ser Asn Ile Val Ile Gly Ile
Gly Asp Lys Ala Leu Lys Ile Asn Trp Tyr Lys Lys Gly
Ser Ser Lipo-DEN-3 DNA sequence (SEQ ID NO: 17):
ATG AAA AAA CTG CTG ATT GCG GCG ATG ATG GCG GCG GCG
CTG GCG GCG TGC AGC CAG GAA GCG AAA CAG GAA GTG AAA
GAA GCG GTG CAG GCG GTG GAA AGC GAT GTG AAA GAT ACC
GCG GGA TTC AAA GGC ATG AGC TAT GCG ATG TGC CTG AAC
ACC TTT GTG CTG AAA AAA GAA GTG AGC GAA ACC CAG CAT
GGC ACC ATT CTG ATT AAA GTG GAA TAT AAA GGC GAA GAT
GCG CCG TGC AAA ATT CCG TTT AGC ACC GAA GAT GGC CAG
GGC AAA GCG CAT AAC GGC CGT CTG ATT ACC GCG AAC CCG
GTG GTG ACC AAA AAA GAA GAA CCG GTG AAC ATT GAA GCG
GAA CCG CCG TTT GGC GAA AGC AAC ATT GTG ATT GGC ATT
GGC GAT AAA GCG CTG AAA ATT AAC TGG TAT AAA AAA GGC
AGC AGC Lipo-DEN-4 Amino acid sequence (SEQ ID NO: 18):
Met Lys Lys Leu Leu Ile Ala Ala Met Met Ala Ala Ala
Leu Ala Ala Cys Ser Gln Glu Ala Lys Gln Glu Val Lys
Glu Ala Val Gln Ala Val Glu Ser Asp Val Lys Asp Thr
Ala Gly Ser Lys Gly Met Ser Tyr Thr Met Cys Ser Gly
Lys Phe Ser Ile Asp Lys Glu Met Ala Glu Thr Gln His
Gly Thr Val Val Lys Val Lys Tyr Glu Gly Ala Gly
Ala Pro Cys Lys Val Pro Ile Glu Ile Arg Asp Val Asn
Lys Glu Lys Val Val Gly Arg Ile Ile Ser Ser Thr Pro
Phe Ala Glu Asn Thr Asn Ser Val Thr Asn Ile Glu Leu
Glu Pro Pro Phe Gly Asp Ser Tyr Ile Val Ile Gly Val
Gly Asp Ser Ala Leu Thr Leu His Trp Phe Arg Lys Gly
Ser Ser Lipo-DEN-4 DNA sequence (SEQ ID NO: 19):
ATG AAA AAA CTG CTG ATT GCG GCG ATG ATG GCG GCG GCG
CTG GCG GCG TGC AGC CAG GAA GCG AAA CAG GAA GTG AAA
GAA GCG GTG CAG GCG GTG GAA AGC GAT GTG AAA GAT ACC
GCG GGA TTC AAA GGC ATG AGC TAT ACC ATG TGC AGC GGC
AAA TTT AGC ATT GAT AAA GAA ATG GCG GAA ACC CAG CAT
GGC ACC ACC GTG GTG AAA GTG AAA TAT GAA GGC GCG GGC
GCG CCG TGC AAA GTG CCG ATT GAA ATT CGT GAT GTG AAC
AAA GAA AAA GTG GTG GGC CGT ATT ATT AGC AGC ACC CCG
TTT GCG GAA AAC ACC AAC AGC GTG ACC AAC ATT GAA CTG
GAA CCG CCG TTT GGC GAT AGC TAT ATT GTG ATT GGC GTG
GGC GAT AGC GCG CTG ACC CTG CAT TGG TTT CGT AAA GGC
AGC AGC
```

The term "lipidating sequence" used herein refers to an amino acid sequence that (a) includes a first fragment that is at least 80% (85%, 90%, 95%, or 99%) identical to SP of Ag473 and a second fragment at least 80% (85%, 90%, 95%, or 99%) identical to Domain 1 of Ag473, the first fragment being at the N-terminus of the lipidating sequence, and (b) facilitates lipidation in *E. coli* of a polypeptide or protein carrying the lipidating sequence at its N-terminus. In the lipidating sequence, the first fragment is linked to the second fragment either directly or via a peptide linker. Preferably, this sequence has a length of 40-100 (e.g., 40-80) amino acids. In one example, the lipidating sequence described herein includes SP and Domain 1, i.e., aa 1-40 of SEQ ID NO: 1 (SEQ ID NO: 20). Other examples of the lipidating sequence include any other fragments of SEQ ID NO: 1 that include aa 1-40, e.g., 1-41, 1-45, 1-50, 1-60, 1-80, 1-100, and 1-121 of SEQ ID NO: 1. Examples also include aa 1-41 and aa 1-42 of SEQ ID NO: 12 (SEQ ID NOs: 21 and 22).

As used herein, "percent homology" of two amino acid sequences is determined using the algorithm described in Karlin and Altschul, *Proc, Natl. Acad. Sci. USA* 87:2264-2268, 1990, modified as described in Karlin and Altschul, *Proc, Natl. Acad. Sci. USA* 90:5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

A fusion protein of the invention can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

In one embodiment of the present invention, the lipidating sequence mentioned above is linked to dengue cED III to form a fusion protein, which is in lipidated form when expressed in *E. coli* by conventional recombinant technology. An example follows. A DNA fragment encoding the lipidating sequence and a DNA fragment encoding the dengue cED III are inserted into an expression vector, preferably carrying a strong promoter (e.g., T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured under suitable conditions for protein expression. It is preferred that the *E. coli* host strain be resistant to the toxic effects induced by over-expression of exogenous proteins. Such *E. coli* strains can be identified/generated by the methods described in U.S. Pat. No. 6,361,966. Examples of these *E. coli* strains include, but are not limited to, C43(DE3) (ECCC B96070445), C41(DE3) (ECCC B96070444), C0214(DE3), DK8(DE3)S(NCIMB 40885), and C2014(DE3) (NCIMB 40884).

Preferably, the fusion protein thus expressed is isolated from the *E. coli* host cells and its lipidation status is confirmed via methods known in the art, e.g., immunoblotting with an anti-lipoprotein antibody or mass spectrometry.

A fusion protein of this invention can also be used to prepare an immunogenic composition (e.g., a vaccine) for generating antibodies against Dengue virus in a subject (e.g., a human subject) susceptible to the virus. Such compositions can be prepared, e.g., in the manners described below, or by any other equivalent methods known in the art.

This lipidated fusion protein can be mixed with a pharmaceutically acceptable carrier such as a phosphate buffered saline, a bicarbonate solution, or an adjuvant to produce a pharmaceutical composition. The carrier must be "acceptable" in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. In one example, the fusion protein is mixed with an adjuvant to form a composition useful for immune modulation. This composition may be prepared as injectables, as liquid solutions or emulsions. See U.S. Pat. Nos. 4,601,903; 4,599,231; 4,599,230; and 4,596,792.

An "adjuvant" refers to a substance added to an immunogenic composition, such as a vaccine, that while not having any specific antigenic effect in itself, can stimulate the immune system and increase the immune response to the immunogenic composition. Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing *Corynebacterium parvum* and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery.

See Audran R. et al. Vaccine 21:1250-5, 2003; and Denis-Mize et al. Cell Immunol., 225:12-20, 2003. Alternatively, the lipo-cED III fusion protein of the invention can be used in a dengue vaccine without any adjuvant.

An effective amount of the pharmaceutical composition described above may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders. An "effective amount" means that amount of a composition that elicits a biological or medicinal response in a tissue system of a subject, or in a subject, that is being sought by a researcher, veterinarian, medical doctor or other clinician.

The above-described fusion protein can be used in an immunogenic composition, e.g., a vaccine for generating antibodies and immune response against Dengue virus in a subject susceptible to the virus. A vaccine can be administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

As described in the examples below, the above-described fusion protein or composition can be used to induce immune response in a subject against Dengue virus infection. The term "immune response" or "immunogenic response" refers to any reaction of the immune system in response to an antigen in a subject. Examples of an immune response in a vertebrate include, but are not limited to, antibody production, induction of cell-mediated immunity, complement activation, and development of immune tolerance. The immune response to a subsequent stimulus by the same antigen, also named the secondary immune response, is more rapid than in the case of the primary immune response.

An "antigen" refers to a molecule containing one or more epitopes that will stimulate a host's immune system to make a humoral and/or cellular antigen-specific response. The term "antigen" is used interchangeably with "immunogen." As a result of coming in contact with appropriate cells, an "antigen" induces a state of sensitivity or immune responsiveness and reacts in a demonstrable way with antibodies or immune cells of the sensitized subject in vivo or in vitro. An "antigen" can be specifically recognized and bound by antibodies in an organism. An antigen in association with a major histocompatibility complex (MHC) can also be recognized and bound by receptors on the surface of T lymphocytes (T-cells), leading to the activation of the T-cells. The term "epitope" as used herein refers to the site on an antigen to which a specific antibody molecule or a T-cell receptor binds. The term "epitope" is used herein interchangeably with "antigenic determinant" or "antigenic determinant site."

A subject susceptible to Dengue virus infection can be identified by methods known in the art and administered a composition of the invention. The dose of the composition depends, for example, on the particular polypeptide/protein, whether an adjuvant is co-administered, and the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the composition against the Dengue virus. Methods of assaying antibodies or cytotoxic T cells against a protein or infection are well known in the art. Additional boosters can be given as needed. By varying the amount of polypeptide/protein, the dose of the composition, and frequency of administration, the immunization protocol can be optimized for eliciting a maximal immune response. Before a large scale administering, efficacy testing is desirable. In an efficacy testing, a non-human subject (e.g., mouse, rat, rabbit, house, pig, cow, or monkey) can be administered via an oral or parenteral route with a composition of the invention. After the initial administration or after optional booster administration, both the test subject and the control subject (receiving mock administration) can be challenged with Dengue virus to test the efficacy of the composition.

This invention also features an isolated antibody, polyclonal or monoclonal, that selectively binds to a peptide comprising a sequence selected from the group consisting of SEQ ID NOs: 6 and 23-26. To produce this antibody of claim 20, one can use standard antibody generating techniques, including immunizing an animal with the above-described fusion protein, which elicits an immune response in the animal to produce the antibody; and isolating the antibody or a cell producing the antibody from the animal The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

Expression of Lipidated Fusion Protein lipo-cED III

The cED III gene was obtained using an assembly PCR method with overlapping primers. The product of the assembly PCR was then amplified by conventional PCR. The forward primer for this step (5'-ACATATGAAAGGCATGAGC-TATGCG-3', SEQ ID NO: 2) included an Nde I site, and the reverse primer (5'-ACTCGAGGCTGCTGCCTTTTTTA-3', SEQ ID NO: 3), included an Xho I site. The PCR product was cloned into the expression vector pET-22b(+) (NOVAGEN, Madison, Wis.), using Nde I and Xho I sites to produce a pDconE3 plasmid. As a result, the C-terminal end of the recombinant protein contains an additional hexahistidine tag (HisTag).

The Ag473 fragments D1 shown in FIG. 1 were obtained by PCR using the primers listed below: D1 forward primer: 5'-GGAATTCCATATGAAAAAATTATTGATTGC-3' (SEQ ID NO: 4); D1 reverse primer: 5'-CGGGATTCCGCAGT-GTCTTTAACATCGGA-3' (SEQ ID NO: 5). The PCR products thus obtained were cloned into the pDconE3 plasmid to produce a pD1E3expression plasmid, which had a sequence (SEQ ID NO: 28) encoding the fusion protein lipo-cED III (SEQ ID NO: 27), shown below:

```
Lipo-cEDIII Amino acid sequence:
Met Lys Lys Leu Leu Ile Ala Ala Met Met Ala Ala Ala
Leu Ala Ala Cys Ser Gln Glu Ala Lys Gln Glu Val Lys
Glu Ala Val Gln Ala Val Glu Ser Asp Val Lys Asp Thr
Ala Gly Ser Lys Gly Met Ser Tyr Ala Met Cys Thr Gly
Lys Phe Lys Leu Glu Lys Glu Val Ala Glu Thr Gln His
Gly Thr Ile Leu Ile Lys Val Lys Tyr Glu Gly Asp Gly
Ala Pro Cys Lys Ile Pro Phe Glu Ile Gln Asp Val Glu
Lys Lys His Val Asn Gly Arg Leu Ile Thr Ala Asn Pro
Ile Val Thr Asp Lys Glu Ser Pro Val Asn Ile Glu Ala
Glu Pro Pro Phe Gly Asp Ser Tyr Ile Val Ile Gly Val
Gly Asp Lys Ala Leu Lys Leu Asn Trp Phe Lys Lys Gly
Ser Ser
(SEQ ID NO: 27; underlined segments: SEQ ID NOs: 20
 and 6 respectively)

Lipo-cEDIII DNA sequence:
                                      (SEQ ID NO: 28)
ATG AAA AAA CTG CTG ATT GCG GCG ATG ATG GCG GCG GCG
CTG GCG GCG TGC AGC CAG GAA GCG AAA CAG GAA GTG AAA
GAA GCG GTG CAG GCG GTG GAA AGC GAT GTG AAA GAT ACC
GCG GGA TTC AAA GGC ATG AGC TAT GCG ATG TGC ACC GGC
AAA TTT AAA CTG GAA AAA GAA GTG GCG GAA ACC CAG CAT
GGC ACC ATT CTG ATT AAA GTG AAA TAT GAA GGC GAT GGC
GCG CCG TGC AAA ATT CCG TTT GAA ATT CAG GAT GTG GAA
AAA AAA CAT GTG AAC GGC CGT CTG ATT ACC GCG AAC CCG
ATT GTG ACC GAT AAA GAA AGC CCG GTG AAC ATT GAA GCG
GAA CCG CCG TTT GGC GAT AGC TAT ATT GTG ATT GGC GTG
```

-continued

```
GGC GAT AAA GCG CTG AAA CTG AAC TGG TTT AAA AAA GGC
AGC AGC
```

The expression plasmids noted above were introduced into *E. coli* strain C43(DE3) (IMAXIO, Saint-Beauzire, France) via conventional recombinant technology and positive transformants were selected. The transformants were cultured at 37° C. overnight and then induced with 1 mM of IPTG for 3 hours. The *E. coli* cells were harvested afterwards by centrifugation and lyzed. The cell lysates were first analyzed by SDS-PAGE to determine presence of the fusion protein, i.e., lipo-cED III expressed from the expression plasmid.

EXAMPLE 2

Characterization of Fusion Protein lipo-cED III

Recombinant cED III, expressed from pDconE3, and fusion protein lipo-cED III, expressed from pD1E3, were isolated from C43(DE3) cells by immobilized metal affinity chromatography (IMAC) as follows. *E. coli* cells were harvested from 2.4 liter cell cultures by centrifugation (8000×g for 20 min) and the pellets thus collected were re-suspended in 100 ml of a homogenization buffer containing 20 mM Tris-Cl (pH 8.0), 500 mM NaCl, 10% glycerol, 50 mM sucrose, and 10 mM imidazole). The *E. coli* cells were then disrupted using a French Press (CONSTANT SYSTEMS, Daventry, UK) at 27 Kpsi in the presence of a detergent and the cell lysates thus obtained were centrifuged at 80,000×g for 60 min. The supernatants were collected and loaded onto a column (2.2 cm i.d.×5.3 cm) filled with 20 ml Ni—NTA resin (QIAGEN, San Diego, Calif., USA). The column was washed first with the homogenization buffer and then with the same buffer containing 50 mM imidazole. The recombinant proteins were eluted with the homogenization buffer containing 500 mM imidazole and characterized by both SDS-PAGE and immunoblotting. The result thus obtained (which is showed in FIG. 2) indicate that recombinant lipo-cED III were isolated with high purity, content of lipopolysaccharide<3EU/mg.

Fusion protein lipo-cED III was then subjected to mass spectrometry (MS) analysis as described below. The protein was first dialyzed against 5 mM ammonium bicarbonate at pH 8.5 and then treated with trypsin (PROMEGA Co., Madison, Wis.) at a lipo-cED III: trypsin ratio of 50:1 (Wt/Wt) in 25 mM ammonium bicarbonate (pH 8.5) for 2 hours at room temperature. The enzymatic reaction was terminated by addition of formic acid (final concentration 1.2%). One microliter of the typsini-digested protein was mixed with 1 μl of a saturated solution of α-ciano-4-hydrozycinnamic acid (SIGMA) in acetonitrile/0.1% trifluoroacetic acid (1:3, vol/vol). One microliter of the mixture was placed on the target plate of a matrix-assisted laser desorption ionization time-of-flight (MALDI-TOF) mass spectrometer (BURKER) for analysis. The MS peaks obtained from this analysis represent the peptides obtained from complete trpsin-digestion of lipo-cED III. These peptides correspond to the C-terminal fragments of the fusion protein. The MS results also indicate that these peptides are not modified.

The fusion protein was then subjected to partial trypsin digestion (10 minutes digestion). Results obtained from MALDI-TOF analysis as described above indicate that the partial trypsin digestion products correspond to the N-terminal fragments of lipo-cED III and these peptides are lipidated. Take together, it is demonstrated that fusion protein lipo-cED III is a lipoprotein.

EXAMPLE 3

Bioactivity of lipo-cED III

To evaluate the immunogenic property of rlipo-cED III in vivo, assays were carried out to analyze the magnitude of cED III-specific antibody responses in mice immunized with either recombinant cED III or recombinant lipo-cED III.

Groups of 8-12-week old BALB/c mice (n=5) were initially immunized subcutaneously with 20 μg (1.5 nmol) of recombinant lipo-cED III, or 20 μg (1.6 nmol) of recombinant cED III formulated in PBS. The antigen of the same formulation and amount was administered subcutaneously to boost the immune response in each mouse on day 14 after priming. Immune sera were collected by tail vein bleeding 2 weeks after the booster immunization. Anti-cED III antibody titers were determined by ELISA. Briefly, microtiter plates were coated with cED III and incubated with the sera of various dilutions. Bound IgG was detected with horseradish peroxidase-conjugated goat anti-mouse IgG Fc. Color was developed by adding 3,3,5,5-tetramethylbenzidine and the absorbance at 450 nm was measured in an ELISA reader. End-point titers were defined as the serum dilution that resulted in an absorbance value>0.2.

Figure 3:
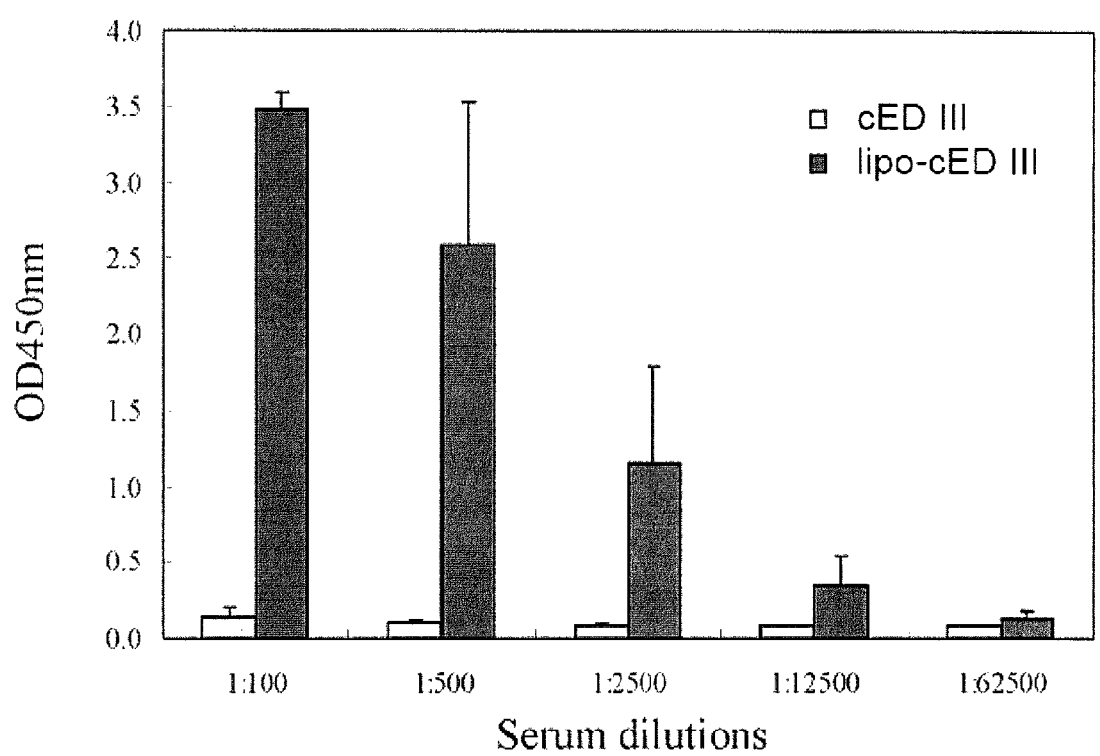
FIG. 3 is a diagram showing the magnitude of the cED III-specific antibody responses in mice immunized with either recombinant cED III or recombinant lipo-cED III.

As shown in FIG. 3, the mice immunized with cED III alone elicited barely detectable levels of anti-cED III IgG antibody responses, whereas the mice immunized with recombinant lipo-cED III without adjuvant generated much higher titers of anti-E3 antibodies. Immunization with recombinant lipo-cED III elicited antibody titers that were 500-fold higher than those obtained with recombinant cED III alone.

To evaluate the ability of recombinant cED III and recombinant lipo-cED III to induce cross-neutralizing antibodies against four serotypes of dengue virus, a foci reduction neutralization assay was performed to test increasing dilutions of pooled individual immune sera from mice of each group.

BALB/c mice (n=5) were immunized subcutaneously with 20 μg/mouse of cED III or lipo-cED III three times at two-week intervals. Sera were collected 14 days after the last immunization. The sera from each group were then pooled to evaluate neutralization of the infectivity of dengue virus by Focus Reduction Neutralization Test (FRNT). The neutralizing antibody titer was calculated as the reciprocal of the highest dilution that resulted in a 40% reduction of Focus-Forming Unit (FFU) compared to that of a control of virus with pre-immunization sera. The neutralizing antibody titers were summarized in Table 1 below.

TABLE 1

Mice immunized with rlipo-cED III developed cross-neutralizing antibodies against four serotypes of dengue virus

|  | cED III | Lipo-cED III |
| --- | --- | --- |
| Dengue-1 | <8 | 16 |
| Dengue-2 | <8 | 16 |
| Dengue-3 | <8 | 8 |
| Dengue-4 | <8 | 16 |

As showed in Table 1, recombinant cED III elicited the lowest neutralizing antibody titer (<8). In contrast, recombinant lipo-cED III, in the absence of adjuvant, generated a cross-neutralizing effect (from 8 to 16). These results demonstrate that the cED III is able to elicit antibodies to inhibit the four serotypes of dengue viral infections when it is lipidated with the aid of a lipidating sequence derived from Ag473.

In the present invention, it is unambiguously demonstrated that fusion of a lipidated domain to dengue cED III can dramatically enhance the immunogenicity of dengue cED III and that the lipidated cED III (lipo-cED III) is much more immunogenic than its non-lipidated counterpart. Furthermore, the observation that recombinant lipo-cED III induced significantly higher neutralizing antibody titers against dengue virus than non-lipidated recombinant cED III counterpart not only indicates that the lipid moiety confers immunopotentiating activity to the fusion protein but also that the additional bacterial sequence did not alter the functional epitope structure of the viral immunogen. Therefore, the present invention provides a new approach for a large-scale production of dengue cED III lipoprotein and lipo-immunogen with intrinsic adjuvant properties for the design of a new generation of dengue virus vaccines.

EXAMPLE 4

Lipidated Den-1 ED III Developed Neutralizing Antibodies Against Dengue-1 Virus To evaluate the ability of recombinant Den-1 ED III and recombinant lipo-Den-1 ED III (SEQ ID NO: 12) to induce neutralizing antibodies against dengue-1 virus, we tested increasing dilutions of pooled individual immune sera from mice using the foci reduction neutralization assay described above.

Briefly, BALB/c mice (n=5) were immunized subcutaneously with 10 μg of Den-1 ED III or lipo-Den-1 ED III three times at two-week intervals. Sera were collected 14 days after the last immunization. The sera in each group were pooled to evaluate neutralization of the infectivity of dengue virus by FRNT. The neutralizing antibody titer was calculated as the reciprocal of the highest dilution that resulted in a 40% reduction of FFU compared to that of a control of virus with pre-immunization sera. Values are the means of triplicate wells. The results were summarized in Table 2.

TABLE 2

Immunized mice with lipo-Den-1 ED III developed neutralizing antibodies against dengue-1 virus.

|  | Den-1 ED III | lipo-Den-1 ED III |
| --- | --- | --- |
| Dengue-1 | <8 | 16 |
| Dengue-2 | <8 | 8 |
| Dengue-3 | 32 | 32 |
| Dengue-4 | 16 | 32 |

EXAMPLE 5

Lipidated Den-2 ED III Developed Neutralizing Antibodies Against Dengue-2 Virus To evaluate the ability of recombinant Den-2 ED III and recombinant lipo-Den-2 ED III (SEQ ID NO: 14) to induce neutralizing antibodies against dengue-2 virus, we tested increasing dilutions of pooled individual immune sera from mice of each group in the foci reduction neutralization assay. BALB/c mice (n=5) were immunized subcutaneously with 10 μg of Den-2 ED III or lipo-Den-2 ED III three times at two-week intervals. Sera were collected 14 days after the last immunization. Sera were pooled in each group to evaluate neutralization of the infectivity of dengue virus by FRNT. The neutralizing antibody titer was calculated as the reciprocal of the highest dilution that resulted in a 40% reduction of FFU compared to that of a control of virus with pre-immunization sera. Values are the means of triplicate wells. The results were summarized in Table 3.

TABLE 3

Immunized mice with lipo-Den-2 ED III developed neutralizing antibodies against dengue-2 virus.

|  | Den-2 ED III | lipo-Den-2 ED III |
|---|---|---|
| Dengue-1 | <8 | 8 |
| Dengue-2 | 8 | >256 |
| Dengue-3 | <8 | <8 |
| Dengue-4 | 8 | 8 |

EXAMPLE 6

Lipidated Den-3 ED III Developed Neutralizing Antibodies Against Dengue-3 Virus

To evaluate the ability of recombinant Den-3 ED III and recombinant lipo-Den-3
ED III (SEQ ID NO: 16) to induce neutralizing antibodies against dengue-3 virus, we tested increasing dilutions of pooled individual immune sera from mice of each group in the foci reduction neutralization assay. BALB/c mice (n=5) were immunized subcutaneously with 10 μg of Den-4 ED III or lipo-Den-4 ED III three times at two-week intervals. Sera were collected 14 days after the last immunization. Sera were pooled in each group to evaluate neutralization of the infectivity of dengue virus by FRNT. The neutralizing antibody titer was calculated as the reciprocal of the highest dilution that resulted in a 40% reduction of FFU compared to that of a control of virus with pre-immunization sera. Values are the means of triplicate wells. The results were summarized in Table 4.

TABLE 4

Immunized mice with lipo-Den-3 ED III developed neutralizing antibodies against dengue-3 virus.

|  | Den-3 ED III | lipo-Den-3 ED III |
|---|---|---|
| Dengue-1 | 8 | 16 |
| Dengue-2 | <8 | <8 |
| Dengue-3 | 8 | 16 |
| Dengue-4 | 8 | 32 |

EXAMPLE 7

Lipidated Den-4 ED III Developed Neutralizing Antibodies Against Dengue-4 Virus

To evaluate the ability of recombinant Den-4 ED III and recombinant lipo-Den-4 ED III (SEQ ID NO: 18) to induce neutralizing antibodies against dengue-4 virus, we tested increasing dilutions of pooled individual immune sera from mice of each group in the foci reduction neutralization assay. BALB/c mice (n=5) were immunized subcutaneously with 10 μg of Den-4 ED III or lipo-Den-4 ED III three times at two-week intervals. Sera were collected 14 days after the last immunization. Sera were pooled in each group to evaluate neutralization of the infectivity of dengue virus by FRNT. The neutralizing antibody titer was calculated as the reciprocal of the highest dilution that resulted in a 40% reduction of FFU compared to that of a control of virus with pre-immunization sera. Values are the means of triplicate wells. The results were summarized in Table 5.

TABLE 5

Immunized mice with lipo-Den-4 ED III developed neutralizing antibodies against dengue-4 virus.

|  | Den-4 ED III | lipo-Den-4 ED III |
|---|---|---|
| Dengue-1 | <8 | <8 |
| Dengue-2 | 16 | 128 |
| Dengue-3 | <8 | <8 |
| Dengue-4 | <8 | >256 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated fusion protein, comprising
 a first segment having a lipidating sequence, the lipidating sequence being at least 80% identical to the sequence of SEQ ID NO: 20 and capable of promoting lipidation of the fusion protein, and
 a second segment having the sequence of a dengue viral protein fragment, wherein the first segment is located at the N-terminus to the second segment in the fusion protein.

2. The fusion protein of claim 1, wherein the fusion protein is lipidated.

3. The fusion protein of claim 1, wherein the lipidating sequence includes the sequence of SEQ ID NO: 20.

4. The fusion protein of claim 3, wherein the lipidating sequence contains the sequence of SEQ ID NO: 21 or 22.

5. The fusion protein of claim 1, wherein the dengue viral protein fragment contains a sequence selected from the group consisting of SEQ ID NOs: 6 and 23-26.

6. The fusion protein of claim 5, wherein the fusion protein contains a sequence selected from the group consisting of SEQ ID NOs: 12, 14, 16, 18, and 27.

7. An immunogenic composition comprising the isolated fusion protein of claim 1, wherein the second segment has the sequence of an immunogenic dengue viral protein fragment and the fusion protein is lipidated.

8. The immunogenic composition of claim 7, wherein the composition further comprises a pharmaceutically acceptable adjuvant.

9. A method of inducing an immune response to dengue virus infection, comprising administering to a subject in need thereof an effective amount of immunogenic composition of claim 7.

10. The method of claim 9, wherein the immunogenic composition is not formulated with an adjuvant.

11. The method of claim 9, wherein the immunogenic composition is formulated with an adjuvant.

12. The fusion protein of claim 1, wherein the lipidating sequence is at least 90% identical to the sequence of SEQ ID NO: 20.

13. The fusion protein of claim 1, wherein the lipidating sequence is at least 95% identical to the sequence of SEQ ID NO: 20.

14. The immunogenic composition of claim 7, wherein the lipidating sequence includes the sequence of SEQ ID NO: 20.

15. The immunogenic composition of claim 7, wherein the dengue viral protein fragment contains a sequence selected from the group consisting of SEQ ID NOs: 6 and 23-26.

16. The immunogenic composition of claim 15, wherein the fusion protein contains a sequence selected from the group consisting of SEQ ID NOs: 12, 14, 16, 18, and 27.

17. The method of claim 9, wherein the lipidating sequence includes the sequence of SEQ ID NO: 20.

18. The method of claim 9, wherein the dengue viral protein fragment contains a sequence selected from the group consisting of SEQ ID NOs: 6 and 23-26.

19. The method of claim 18, wherein the fusion protein contains a sequence selected from the group consisting of SEQ ID NOs: 12, 14, 16, 18, and 27.

* * * * *

SEQUENCE LISTING

```
<160> NUMBER OF SEQ ID NOS: 28

<210> SEQ ID NO 1
<211> LENGTH: 121
<212> TYPE: PRT
<213> ORGANISM: Neisseria meningitidis

<400> SEQUENCE: 1

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30
```

-continued

```
Glu Ser Asp Val Lys Asp Thr Ala Ala Ser Ala Ala Glu Ser Ala Ala
        35                  40                  45
Ser Ala Val Glu Glu Ala Lys Asp Gln Val Lys Asp Ala Ala Ala Asp
    50                  55                  60
Ala Lys Ala Ser Ala Glu Glu Val Thr Glu Ala Lys Glu Ala Val
65                  70                  75                  80
Thr Glu Ala Lys Glu Ala Val Thr Glu Ala Lys Glu Ala Val Thr Glu
                85                  90                  95
Ala Ala Lys Asp Thr Leu Asn Lys Ala Ala Asp Ala Thr Gln Glu Ala
            100                 105                 110
Ala Asp Lys Met Lys Asp Ala Ala Lys
            115                 120

<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
acatatgaaa ggcatgagct atgcg                                          25

<210> SEQ ID NO 3
<211> LENGTH: 23
<212> TYPE: DNA
<213> ORGANISM: Artificial sequence
<220> FEATURE:
<223> OTHER INFORMATION: Synthetic primer

<400> SEQUENCE: 3
actcgaggct gctgcctttt tta                                            23

<210> SEQ ID NO 4
<211> LENGTH: 30
<212> TYPE: DNA
<213> ORGANISM: Artificial sequence
<220> FEATURE:
<223> OTHER INFORMATION: Synthetic primer

<400> SEQUENCE: 4
ggaattccat atgaaaaaat tattgattgc                                     30

<210> SEQ ID NO 5
<211> LENGTH: 29
<212> TYPE: DNA
<213> ORGANISM: Artificial sequence
<220> FEATURE:
<223> OTHER INFORMATION: Synthetic primer

<400> SEQUENCE: 5
cgggattccg cagtgtcttt aacatcgga                                      29

<210> SEQ ID NO 6
<211> LENGTH: 103
<212> TYPE: PRT
<213> ORGANISM: Dengue virus

<400> SEQUENCE: 6

Lys Gly Met Ser Tyr Ala Met Cys Thr Gly Lys Phe Lys Leu Glu Lys
1               5                   10                  15
Glu Val Ala Glu Thr Gln His Gly Thr Ile Leu Ile Lys Val Lys Tyr
            20                  25                  30
```

```
Glu Gly Asp Gly Ala Pro Cys Lys Ile Pro Phe Glu Ile Gln Asp Val
            35                  40                  45

Glu Lys Lys His Val Asn Gly Arg Leu Ile Thr Ala Asn Pro Ile Val
 50                  55                  60

Thr Asp Lys Glu Ser Pro Val Asn Ile Glu Ala Glu Pro Pro Phe Gly
 65                  70                  75                  80

Asp Ser Tyr Ile Val Ile Gly Val Gly Asp Lys Ala Leu Lys Leu Asn
                 85                  90                  95

Trp Phe Lys Lys Gly Ser Ser
            100

<210> SEQ ID NO 7
<211> LENGTH: 309
<212> TYPE: DNA
<213> ORGANISM: Dengue virus

<400> SEQUENCE: 7
aaaggcatga gctatgcgat gtgcaccggc aaatttaaac tggaaaaaga agtggcggaa      60
acccagcatg gcaccattct gattaaagtg aaatatgaag gcgatggcgc gccgtgcaaa     120
attccgtttg aaattcagga tgtggaaaaa aaacatgtga acggccgtct gattaccgcg     180 aaccccgattg tgaccgataa agaaagcccg gtgaacattg aagcggaacc gccgtttggc     240
gatagctata ttgtgattgg cgtgggcgat aaagcgctga aactgaactg gtttaaaaaa     300
ggcagcagc                                                             309

<210> SEQ ID NO 8
<211> LENGTH: 17
<212> TYPE: PRT
<213> ORGANISM: Artificial sequence
<220> FEATURE:
<223> OTHER INFORMATION: A fragment (aa 1-17) of Ag473, a Neisseria
      Mengitidis lipoprotein

<400> SEQUENCE: 8

Met Lys Lys Leu Leu Ile Ala Ala Met Met Ala Ala Ala Leu Ala Ala
  1               5                  10                  15

Cys

<210> SEQ ID NO 9
<211> LENGTH: 23
<212> TYPE: PRT
<213> ORGANISM: Artificial sequence
<220> FEATURE:
<223> OTHER INFORMATION: A fragment (aa 18-40) of Ag473, a Neisseria
      Mengitidis lipoprotein

<400> SEQUENCE: 9

Ser Gln Glu Ala Lys Gln Glu Val Lys Glu Ala Val Gln Ala Val Glu
  1               5                  10                  15

Ser Asp Val Lys Asp Thr Ala
            20

<210> SEQ ID NO 10
<211> LENGTH: 31
<212> TYPE: PRT
<213> ORGANISM: Artificial sequence
<220> FEATURE:
<223> OTHER INFORMATION: A fragment (aa 41-71) of Ag473, a Neisseria
      Mengitidis lipoprotein

<400> SEQUENCE: 10

Ala Ser Ala Ala Glu Ser Ala Ala Ser Ala Val Glu Glu Ala Lys Asp
```

```
                    1               5                  10                 15
Gln Val Lys Asp Ala Ala Asp Ala Lys Ser Ala Glu Glu
            20                  25                 30

<210> SEQ ID NO 11
<211> LENGTH: 50
<212> TYPE: PRT
<213> ORGANISM: Artificial sequence
<220> FEATURE:
<223> OTHER INFORMATION: A fragment (aa 72-121) of Ag473, a Neisseria
      Mengitidis lipoprotein

<400> SEQUENCE: 11

Ala Val Thr Glu Ala Lys Glu Ala Val Thr Glu Ala Lys Glu Ala Val
1               5                  10                 15

Thr Glu Ala Lys Glu Ala Val Thr Glu Ala Ala Lys Asp Thr Leu Asn
            20                  25                 30

Lys Ala Ala Asp Ala Thr Gln Glu Ala Ala Asp Lys Met Lys Asp Ala
        35                  40                 45

Ala Lys
    50

<210> SEQ ID NO 12
<211> LENGTH: 145
<212> TYPE: PRT
<213> ORGANISM: Artificial sequence
<220> FEATURE:
<223> OTHER INFORMATION: A polypeptide having a N-terminal fragment
      (aa 1-40) of Ag473 from Neisseria Mengitidis fused to a fragment
      (aa 43-145) of E3 from Dengue-1

<400> SEQUENCE: 12

Met Lys Lys Leu Leu Ile Ala Ala Met Met Ala Ala Leu Ala Ala
1               5                  10                 15

Cys Ser Gln Glu Ala Lys Gln Glu Val Lys Glu Ala Val Gln Ala Val
            20                  25                 30

Glu Ser Asp Val Lys Asp Thr Ala Gly Ser Lys Gly Met Ser Tyr Val
        35                  40                 45

Met Cys Thr Gly Ser Phe Lys Leu Glu Lys Glu Val Ala Glu Thr Gln
    50                  55                 60

His Gly Thr Val Leu Val Gln Val Lys Tyr Glu Gly Thr Asp Ala Pro
65                  70                  75                  80

Cys Lys Ile Pro Phe Ser Ser Gln Asp Glu Lys Gly Val Thr Gln Asn
                85                  90                 95

Gly Arg Leu Ile Thr Ala Asn Pro Ile Val Thr Asp Lys Glu Lys Pro
            100                 105                110

Val Asn Ile Glu Ala Glu Pro Pro Phe Gly Glu Ser Tyr Ile Val Val
        115                 120                125

Gly Ala Gly Glu Lys Ala Leu Lys Leu Ser Trp Phe Lys Lys Gly Ser
    130                 135                 140

Ser
145

<210> SEQ ID NO 13
<211> LENGTH: 435
<212> TYPE: DNA
<213> ORGANISM: Artificial sequence
<220> FEATURE:
<223> OTHER INFORMATION: A DNA sequence coding a polypeptide having a
      N-terminal fragment (aa 1-40) of Ag473 from Neisseria Mengitidis
      fused to a fragment (aa 43-145) of E3 from Dengue-1
```

<400> SEQUENCE: 13

```
atgaaaaaac tgctgattgc ggcgatgatg gcggcggcgc tggcggcgtg cagccaggaa      60
gcgaaacagg aagtgaaaga agcggtgcag gcggtggaaa gcgatgtgaa agataccgcg     120
ggattcaaag gcatgagcta tgtgatgtgc accggcagct ttaaactgga aaagaagtg     180 gcggaaaccc agcatggcac cgtgctggtg caggtgaaat atgaaggcac cgatgcgccg     240
tgcaaaattc cgtttagcag ccaggatgaa aaaggcgtga cccagaacgg ccgtctgatt     300
accgcgaacc cgattgtgac cgataaagaa aaaccggtga acattgaagc ggaaccgccg     360
tttggcgaaa gctatattgt ggtgggcgcg ggcgaaaaag cgctgaaact gagctggttt     420
aaaaaaggca gcagc                                                      435
```

<210> SEQ ID NO 14
<211> LENGTH: 145
<212> TYPE: PRT
<213> ORGANISM: Artificial sequence
<220> FEATURE:
<223> OTHER INFORMATION: A polypeptide having a N-terminal fragment
       (aa 1-40) of Ag473 from Neisseria Mengitidis fused to a fragment
       (aa 43-145) of E3 from Dengue-2

<400> SEQUENCE: 14

```
Met Lys Lys Leu Leu Ile Ala Ala Met

```
tgcaaaattc cgtttgaaat tatggatctg gaaaaacgtc atgtgctggg ccgtctgatt      300
accgtgaacc cgattgtgac cgaaaaagat agcccggtga acattgaagc ggaaccgccg      360
tttggcgata gctatattat tattggcgtg aaccgggcc agctgaaact gaactggttt      420
aaaaaaggca gcagc                                                      435
```

<210> SEQ ID NO 16
<211> LENGTH: 145
<212> TYPE: PRT
<213> ORGANISM: Artificial sequence
<220> FEATURE:
<223> OTHER INFORMATION: A polypeptide having a N-terminal fragment
      (aa 1-40) of Ag473 from Neisseria Mengitidis fused to a fragment
      (aa 43-145) of E3 from Dengue-3

<400> SEQUENCE: 16

```
Met Lys Lys Leu Leu Ile Ala Ala Met Met Ala Ala Ala Leu

```
<211> LENGTH: 145
<212> TYPE: PRT
<213> ORGANISM: Artificial sequence
<220> FEATURE:
<223> OTHER INFORMATION: A polypeptide having a N-terminal fragment
      (aa 1-40) of Ag473 from Neisseria Mengitidis fused to a fragment
      (aa 43-145) of E3 from Dengue-4

<400> SEQUENCE: 18

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
                20                  25                  30

Glu Ser Asp Val Lys Asp Thr Ala Gly Ser Lys Gly Met Ser Tyr Thr
            35                  40                  45

Met Cys Ser Gly Lys Phe Ser Ile Asp Lys Glu Met Ala Glu Thr Gln
    50                  55                  60

His Gly Thr Thr Val Val Lys Val Lys Tyr Glu Gly Ala Gly Ala Pro
65                  70                  75                  80

Cys Lys Val Pro Ile Glu Ile Arg Asp Val Asn Lys Glu Lys Val Val
                85                  90                  95

Gly Arg Ile Ile Ser Ser Thr Pro Phe Ala Glu Asn Thr Asn Ser Val
            100                 105                 110

Thr Asn Ile Glu Leu Glu Pro Pro Phe Gly Asp Ser Tyr Ile Val Ile
        115                 120                 125

Gly Val Gly Asp Ser Ala Leu Thr Leu His Trp Phe Arg Lys Gly Ser
    130                 135                 140

Ser
145

<210> SEQ ID NO 19
<211> LENGTH: 435
<212> TYPE: DNA
<213> ORGANISM: Artificial sequence
<220> FEATURE:
<223> OTHER INFORMATION: A DNA sequence coding a polypeptide having a
      N-terminal fragment (aa 1-40) of Ag473 from Neisseria Mengitidis
      fused to a fragment (aa 43-145) of E3 from Dengue-4

<400> SEQUENCE: 19
atgaaaaaac tgctgattgc ggcgatgatg gcggcggcgc tggcggcgtg cagccaggaa      60
gcgaaacagg aagtgaaaga agcggtgcag gcggtggaaa gcgatgtgaa agataccgcg     120
ggattcaaag gcatgagcta taccatgtgc agcggcaaat ttagcattga taagaaatg      180 gcggaaaccc agcatggcac caccgtggtg aaagtgaaat atgaaggcgc gggcgcgccg     240
tgcaaagtgc cgattgaaat tcgtgatgtg aacaaagaaa aagtggtggg ccgtattatt     300
agcagcaccc cgtttgcgga aaacaccaac agcgtgacca acattgaact ggaaccgccg     360
tttggcgata gctatattgt gattggcgtg ggcgatagcg cgctgaccct gcattggttt     420
cgtaaaggca gcagc                                                     435

<210> SEQ ID NO 20
<211> LENGTH: 40
<212> TYPE: PRT
<213> ORGANISM: Artificial sequence
<220> FEATURE:
<223> OTHER INFORMATION: A fragment (aa 1-40) of Ag473, a Neisseria
      Mengitidis lipoprotein

<400> SEQUENCE: 20

Met Lys Lys Leu Leu Ile Ala Ala Met Met Ala Ala Ala Leu Ala Ala
```

```
                1               5                  10                 15
Cys Ser Gln Glu Ala Lys Gln Glu Val Lys Glu Ala Val Gln Ala Val
                20                 25                 30

Glu Ser Asp Val Lys Asp Thr Ala
        35                  40

<210> SEQ ID NO 21
<211> LENGTH: 41
<212> TYPE: PRT
<213> ORGANISM: Artificial sequence
<220> FEATURE:
<223> OTHER INFORMATION: A fragment (aa 1-40) of Ag473, a Neisseria
      Mengitidis lipoprotein with an additional glycine at C-terminus

<400> SEQUENCE: 21

Met Lys Lys Leu Leu Ile Ala Ala Met Met Ala Ala Leu Ala Ala
1               5                  10                 15

Cys Ser Gln Glu Ala Lys Gln Glu Val Lys Glu Ala Val Gln Ala Val
                20                 25                 30

Glu Ser Asp Val Lys Asp Thr Ala Gly
        35                  40

<210> SEQ ID NO 22
<211> LENGTH: 42
<212> TYPE: PRT
<213> ORGANISM: Artificial sequence
<220> FEATURE:
<223> OTHER INFORMATION: A fragment (aa 1-40) of Ag473, a Neisseria
      Mengitidis lipoprotein with two additional anino acids (i.e., Gly
      and Ser) at C-terminus

<400> SEQUENCE: 22

Met Lys Lys Leu Leu Ile Ala Ala Met Met Ala Ala Leu Ala Ala
1               5                  10                 15

Cys Ser Gln Glu Ala Lys Gln Glu Val Lys Glu Ala Val Gln Ala Val
                20                 25                 30

Glu Ser Asp Val Lys Asp Thr Ala Gly Ser
        35                  40

<210> SEQ ID NO 23
<211> LENGTH: 103
<212> TYPE: PRT
<213> ORGANISM: Artificial sequence
<220> FEATURE:
<223> OTHER INFORMATION: a fragment (aa 43-145) of E3 from Dengue-1

<400> SEQUENCE: 23

Lys Gly Met Ser Tyr Val Met Cys Thr Gly Ser Phe Lys Leu Glu Lys
1               5                  10                 15

Glu Val Ala Glu Thr Gln His Gly Thr Val Leu Val Gln Val Lys Tyr
                20                 25                 30

Glu Gly Thr Asp Ala Pro Cys Lys Ile Pro Phe Ser Ser Gln Asp Glu
        35                  40                 45

Lys Gly Val Thr Gln Asn Gly Arg Leu Ile Thr Ala Asn Pro Ile Val
    50                  55                 60

Thr Asp Lys Glu Lys Pro Val Asn Ile Glu Ala Glu Pro Pro Phe Gly
65                  70                 75                 80

Glu Ser Tyr Ile Val Val Gly Ala Gly Glu Lys Ala Leu Lys Leu Ser
                85                 90                 95

Trp Phe Lys Lys Gly Ser Ser
            100
```

```
<210> SEQ ID NO 24
<211> LENGTH: 103
<212> TYPE: PRT
<213> ORGANISM: Artificial sequence
<220> FEATURE:
<223> OTHER INFORMATION: a fragment (aa 43-145) of E3 from Dengue-2

<400> SEQUENCE: 24

Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Val Glu Pro Gly Gln Leu Lys Leu Asn
                85                  90                  95

Trp Phe Lys Lys Gly Ser Ser
                100

<210> SEQ ID NO 25
<211> LENGTH: 103
<212> TYPE: PRT
<213> ORGANISM: Artificial sequence
<220> FEATURE:
<223> OTHER INFORMATION: a fragment (aa 43-145) of E3 from Dengue-3

<400> SEQUENCE: 25

Lys Gly Met Ser Tyr Ala Met Cys Leu Asn Thr Phe Val Leu Lys Lys
1               5                   10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95

Trp Tyr Lys Lys Gly Ser Ser
                100

<210> SEQ ID NO 26
<211> LENGTH: 103
<212> TYPE: PRT
<213> ORGANISM: Artificial sequence
<220> FEATURE:
<223> OTHER INFORMATION: a fragment (aa 43-145) of E3 from Dengue-4

<400> SEQUENCE: 26

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45
```

Asn Lys Glu Lys Val Val Gly Arg Ile Ile Ser Ser Thr Pro Phe Ala
              50                  55                  60

Glu Asn Thr Asn Ser Val Thr Asn Ile Glu Leu Glu Pro Pro Phe Gly
 65                  70                  75                  80

Asp Ser Tyr Ile Val Ile Gly Val Gly Asp Ser Ala Leu Thr Leu His
                 85                  90                  95

Trp Phe Arg Lys Gly Ser Ser
            100

<210> SEQ ID NO 27
<211> LENGTH: 145
<212> TYPE: PRT
<213> ORGANISM: Artificial sequence
<220> FEATURE:
<223> OTHER INFORMATION: A polypeptide having a N-terminal fragment
      (aa 1-40) of Ag473 from Neisseria Mengitidis fused to cED III
      from Dengue virus

<400> SEQUENCE: 27

Met Lys Lys Leu Leu Ile Ala Ala Met Met Ala Ala Ala Leu Ala Ala
 1               5                  10                  15

Cys Ser Gln Glu Ala Lys Gln Glu Lys Glu Ala Val Gln Ala Val
                 20                  25                  30

Glu Ser Asp Val Lys Asp Thr Ala Gly Ser Lys Gly Met Ser Tyr Ala
                 35                  40                  45

Met Cys Thr Gly Lys Phe Lys Leu Glu Lys Glu Val Ala Glu Thr Gln
 50                  55                  60

His Gly Thr Ile Leu Ile Lys Val Lys Tyr Glu Gly Asp Gly Ala Pro
 65                  70                  75                  80

Cys Lys Ile Pro Phe Glu Ile Gln Asp Val Glu Lys Lys His Val Asn
                 85                  90                  95

Gly Arg Leu Ile Thr Ala Asn Pro Ile Val Thr Asp Lys Glu Ser Pro
            100                 105                 110

Val Asn Ile Glu Ala Glu Pro Pro Phe Gly Asp Ser Tyr Ile Val Ile
        115                 120                 125

Gly Val Gly Asp Lys Ala Leu Lys Leu Asn Trp Phe Lys Lys Gly Ser
    130                 135                 140

Ser
145

<210> SEQ ID NO 28
<211> LENGTH: 435
<212> TYPE: DNA
<213> ORGANISM: Artificial sequence
<220> FEATURE:
<223> OTHER INFORMATION: A DNA sequence coding a polypeptide having a
      N-terminal fragment (aa 1-40) of Ag473 from Neisseria Mengitidis
      fused to cED III from Dengue virus

<400> SEQUENCE: 28
atgaaaaaac tgctgattgc ggcgatgatg gcggcggcgc tggcggcgtg cagccaggaa      60
gcgaaacagg aagtgaaaga gcggtgcagg cggtggaaa gcgatgtgaa agataccgcg     120
ggattcaaag gcatgagcta tgcgatgtgc accggcaaat ttaaactgga aaagaagtg     180 gcggaaaccc agcatggcac cattctgatt aaagtgaaat atgaaggcga tggcgcgccg     240
tgcaaaattc cgtttgaaat tcaggatgtg gaaaaaaaac atgtgaacgg ccgtctgatt     300

-continued

```
accgcgaacc cgattgtgac cgataaagaa agcccggtga acattgaagc ggaaccgccg    360
tttggcgata gctatattgt gattggcgtg ggcgataaag cgctgaaact gaactggttt    420
aaaaaaggca gcagc                                                     435
```